United States Patent [19]
Donehoo et al.

[11] Patent Number: 5,788,644
[45] Date of Patent: Aug. 4, 1998

[54] AUTOMATIC LEAD SWITCHING FOR ECG MONITOR

[75] Inventors: Robert F. Donehoo, Lutz; Judith A. Clifford, Tampa; Don D. Carr, St. Petersburg, all of Fla.

[73] Assignee: Johnson & Johnson Medical Inc., Tampa, Fla.

[21] Appl. No.: 727,369

[22] Filed: Oct. 8, 1996

[51] Int. Cl.$^6$ ............................................. A61B 5/0428
[52] U.S. Cl. ............................................. 600/509
[58] Field of Search ............................ 128/696, 901; 600/509

[56] References Cited

U.S. PATENT DOCUMENTS

| | | | |
|---|---|---|---|
| 4,577,639 | 3/1986 | Simon et al. | 128/696 |
| 5,022,404 | 6/1991 | Hafner . | |
| 5,025,808 | 6/1991 | Hafner | 128/696 |
| 5,333,617 | 8/1994 | Hafner . | |
| 5,582,181 | 12/1996 | Ruess | 128/696 |

OTHER PUBLICATIONS

"The electrocardiograph" by authors Clark, et al., John G. Webster, editor, *Medical instrumentation—Application and design*, Section 6.2, pp. 275–284.

*Primary Examiner*—William E. Kamm
*Assistant Examiner*—George R. Evanisko
*Attorney, Agent, or Firm*—Woodcock Washburn Kurtz Mackiewicz & Norris LLP

[57] ABSTRACT

A multi-lead ECG monitor which determines whether the reference electrode has been disconnected and, if so, switches to another reference electrode to continue ECG monitoring. Disconnection of the reference electrode can be determined by observing that no ECG signal is being received from any of the electrodes. When this is detected, the reference electrode is switched to another electrode which is selected in accordance with a predetermined priority scheme. After a stabilization period, the system then determines if any electrodes are still connected. If not, then, as before, it is determined that the new reference electrode is not connected and that a new reference electrode needs to be selected. The switching of the reference electrode continues in this manner until it is determined that electrodes are connected. If sufficient electrodes including the new reference electrode are still connected to the patient to permit ECG monitoring, then ECG monitoring continues and a status message is presented to the operator identifying which electrodes are disconnected. Once complete electrode connection is regained, the ECG monitor automatically switches back to the preferred settings with the desired reference electrode.

20 Claims, 4 Drawing Sheets

CHEST LEAD V

5 ELECTRODES: TYPICAL

Fig. 1

CHEST LEADS $V_1$-$V_6$

PRECORDIAL POSITIONS FOR 6 ELECTRODES

Fig. 2

ECG LEAD MANAGEMENT

Fig. 5

AUTOMATIC LEAD SWITCHING FOR ECG MONITOR

BACKGROUND OF THE INVENTION

1. Field of the Invention

The present invention relates to an automatic lead switching system for an electrocardiogram (ECG) monitor, and more particularly, to a system which allows monitoring of the patient's electrocardiogram to continue, even when the reference electrode becomes disconnected, by automatically selecting another electrode to be the reference electrode for continued monitoring.

2. Brief Description of the Prior Art

ECG monitors in the prior art rely on electrode connections to provide the necessary signals to generate the standard ECG waveforms. These electrodes collect differential voltage data and provide the resulting data in what are conventionally called "leads" which are connected to the patient in predetermined configurations to maximize the differential basis for the measured changes in electrical potential occurring during the patient's heartbeat. As known to those skilled in the art, a tracing of the measured electrical potentials is referred to as the patient's electrocardiogram. A general description of ECG tracing is provided by, for example, John G. Webster in Chapter 6 of a text entitled *Medical Instrumentation Application and Design*, Houghton & Mifflin, 1978, starting at page 275.

Figure 1:
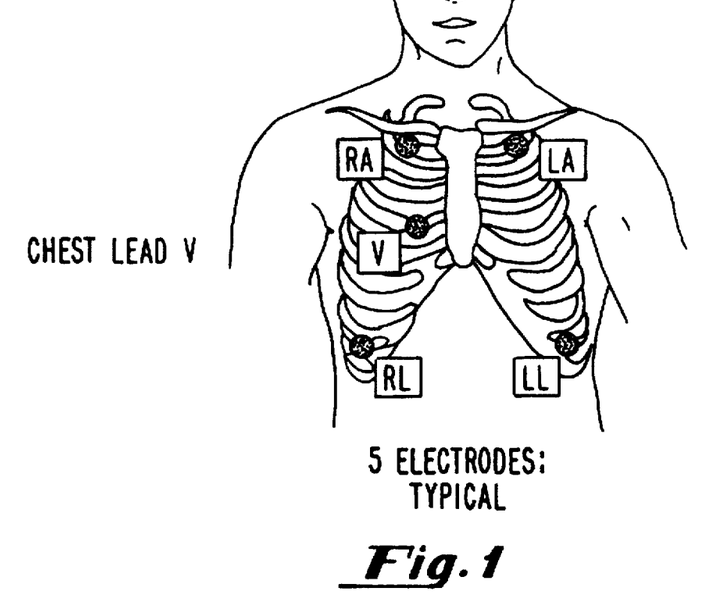
FIG. 1 illustrates a conventional configuration of ECG leads on a patient for monitoring with a typical 5 electrode ECG monitor.
Figure 2:
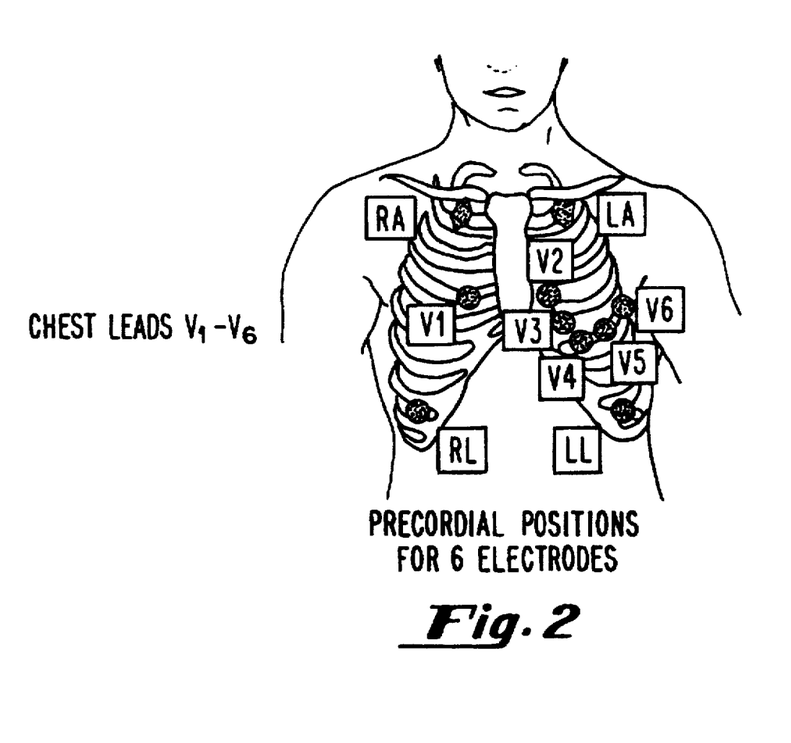
FIG. 2 illustrates several possible conventional configurations of ECG leads on a patient for monitoring with a typical 6 electrode ECG monitor.

In conventional three electrode ECG systems, the ECG leads are placed on the patient's torso proximal to the patient's right arm (the "RA" lead), proximal to the patient's left leg (the "LL" lead), and proximal to the patient's left art (the "LA" lead). Typically, the RA and LL leads are used to generate the detection signal, while the LA lead is the "reference" or "driven" electrode which applies a current to the patient for measurement by the other leads. In multi-lead ECG systems (i.e., those ECG systems having 4, 5, 6, or more electrodes), on the other hand, a lead is also placed on the patient's torso proximal to the right leg (the "RL" lead) and is used as the reference electrode, while the RA, LA, LL, and any other chest leads are used to generate the ECG waveforms. FIG. 1 illustrates a conventional configuration of ECG leads on a patient for monitoring with a typical 5 electrode ECG monitor, where the V electrode is a chest lead, while FIG. 2 illustrates several possible conventional locations of chest lead electrodes used with a typical ECG monitor which monitors a patient with five or more electrodes. In FIG. 2, a plurality of options for placement of the chest leads V1–V6 are illustrated. Placement of the two chest leads is determined from these options by the operator of the ECG monitor based on the possible irregularities to be detected.

Unfortunately, problems occur during ECG monitoring when the ECG leads become disconnected from the patient as a result of patient movement, a poor connection, and the like. If the electrode which comes disconnected is one of the detection electrodes, no ECG signal is provided that requires the disconnected electrode. However, if the reference electrode (typically the RL electrode) becomes disconnected, conventional ECG monitors either lose all monitoring function due to the inability to detect the presence of the connections of the other electrodes, or suffer from noise in the ECG signals due to the inability to apply a common mode signal to the reference electrode. Thus, once the reference electrode is disconnected, conventional ECG systems also lose the ability to detect which other electrodes are connected to or disconnected from the patient.

Accordingly, an ECG monitor is desired which allows ECG monitoring to continue even when the reference electrode becomes disconnected and which allows a determination to be made as to which electrodes are still connected to the patient. The present invention has been designed to meet these needs.

SUMMARY OF THE INVENTION

The present invention relates to an ECG monitor which allows monitoring of the patient's ECG to continue even when the reference electrode becomes disconnected. In short, when the ECG monitor detects that all electrodes have become disconnected, as when the reference electrode is disconnected, another electrode is selected as the reference electrode and receives the driving signal. ECG monitoring then resumes with the remainder of the electrodes until such time as complete electrode status is returned.

A multi-lead ECG monitor in accordance with a preferred embodiment of the invention determines whether the reference electrode becomes disconnected by observing that all electrodes appear to be disconnected. At this time, the reference electrode is switched to another electrode. The new reference electrode is selected in accordance with a predetermined priority scheme which determines which electrode should be the new reference electrode. After a stabilization period, the system then determines if any electrodes are connected. If not, then, as before, it is determined that the new reference electrode is not connected and that a new reference electrode needs to be selected. The switching of the reference electrode continues in this manner until it is determined that an electrode is connected or that all electrodes are in fact disconnected. If sufficient electrodes including the new reference electrode are still connected to the patient to permit ECG monitoring, then ECG monitoring continues and a status message is presented to the operator identifying which electrode(s) is/are disconnected. Once complete electrode connection is regained, the ECG monitor of the invention automatically switches back to the preferred settings with the desired reference electrode. The ECG monitor of the invention thus maintains the ECG monitoring of the patient with a nonstandard reference electrode until such time that complete ECG electrode status is returned.

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings of which.

DETAILED DESCRIPTION OF PRESENTLY PREFERRED EMBODIMENTS

An ECG monitor with the above-mentioned beneficial features in accordance with a presently preferred exemplary embodiment of the invention will be described below with reference to FIGS. 1–5. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

The present invention relates to an ECG monitor. In a preferred embodiment, the ECG monitor of the invention is implemented in a modular patient monitor, such as the DINAMAP™ MPS Select Monitor, available from Johnson & Johnson Medical Inc. The DINAMAP™ Multi Parameter System (MPS) Select Monitor accepts any of a plurality (e.g., nine) of electronics modules which monitor different vital signs of the patient. The respective electronics modules are removably connected to the monitor during use to selectively monitor a patient's vital signs by collecting patient data such as $CO_2$ exhaled by the patient, the patient's heart rate, the patient's blood pressure (invasive or noninvasive), the patient's temperature, the patient's electrocardiogram, the oxygen saturation ($SpO_2$) of the patient's arterial blood, and/or the patient's respiration rate. The respective electronics modules process data from transducers to generate waveforms and numeric data which is processed in a data acquisition unit for display on a monitor for use by the clinician in diagnosing the patient's condition. The present invention is preferably implemented as part of the ECG module in such a system.

When electrocardiographic (ECG) monitoring is desired, the operator first plugs the ECG module into the data acquisition unit of the MPS Select Monitor. Using appropriate medical criteria, the operator then selects electrode sites on the patient. If only three electrodes are to be used, the leads are typically placed in a standard LA, RA, and LL configuration as shown in FIG. 1. However, if 5 or 6 or more leads are used, then the V (chest) electrodes may be placed in any of the six precordial positions shown in FIG. 2, based on the characteristics to be monitored. Prior to application of the electrodes to the patient, the patient's skin is prepared and the lead wires are connected to the electrodes. After application of the electrodes to the patient, the electrode lead wires are plugged into a patient cable connector, and the cable connector is plugged into a parameter input port of the ECG module. The ECG monitoring feature is then selected from the main menu of the MPS Select Monitor and monitoring of the desired ECG waveform parameters begins. If a three electrode configuration is selected, ECG waveforms for a single limb lead are selectable among leads I, II, or III, and one waveform is displayed as the primary lead in a conventional fashion. However, if a four, five, or six electrode configuration is selected, ECG waveforms for leads I, II, III, $aV_R$, $aV_L$, $aV_F$, are derived, and, for five or six electrode configurations, optional chest leads allow CA and CB to be derived. Any of these leads may be chosen as the primary lead, and in the five or six electrode configurations, any lead besides the primary lead may be chosen as a secondary lead. Leads can be changed without changing electrode sites.

Preferably, the ECG module of the invention has audible and visible alarms which lets the operator know when a lead is disconnected and warns the operator of alarm conditions. A lead fail detector in accordance with the invention is also activated when the multiple lead feature is selected (i.e., when four or more leads are selected). As will be explained in more detail below, the loss of all lead ECG signals will trigger a lead failure message, and the primary lead will be automatically switched to another available lead for continued monitoring. A message will also be displayed indicating which electrode has failed. If the primary lead becomes available again, the ECG module of the invention will switch back to that lead as the primary lead unless the operator has in the meantime selected another lead as the primary lead.

Figure 3:
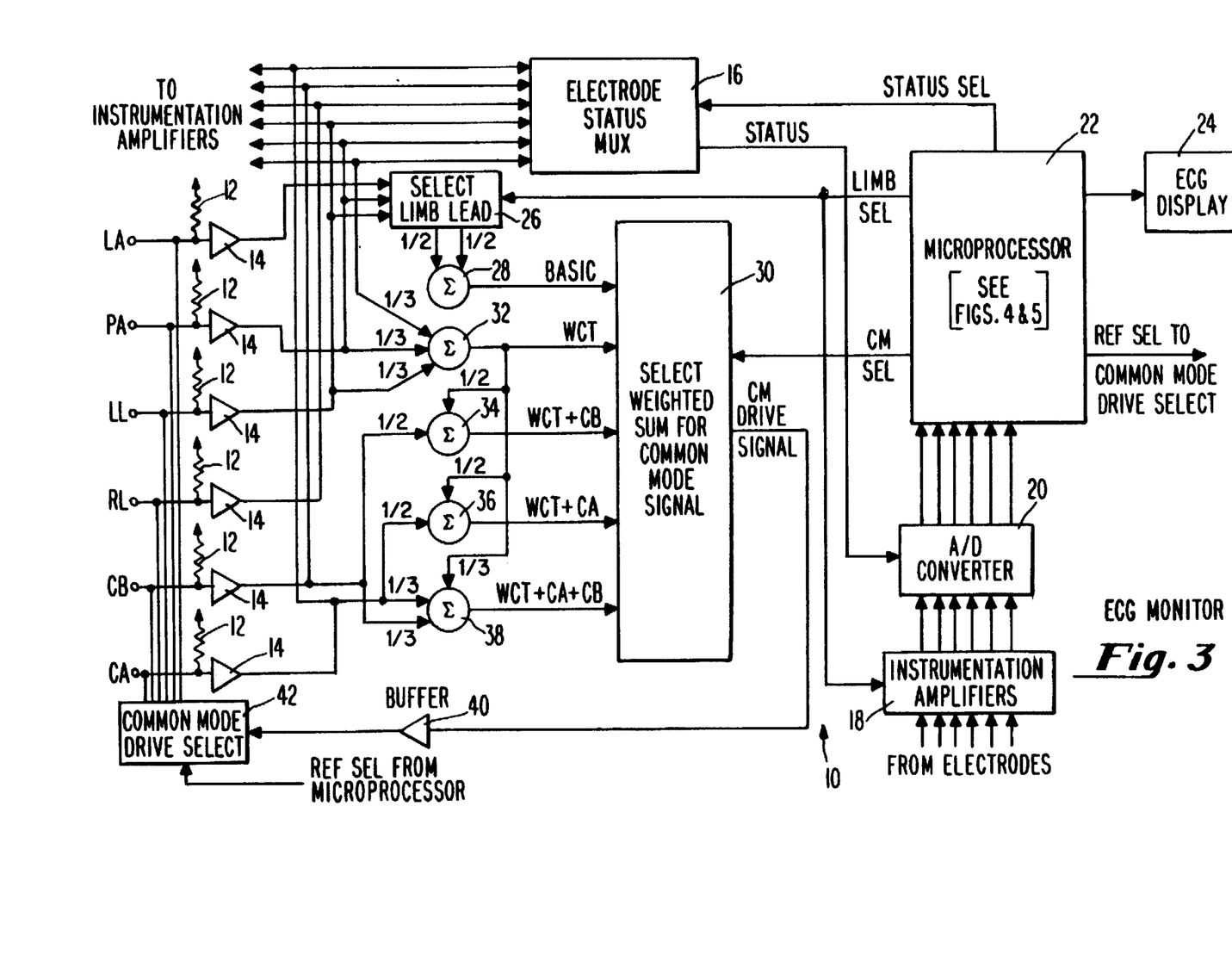
FIG. 3 is a block circuit diagram of an ECU monitor in accordance with a preferred embodiment of the invention.

FIG. 3 illustrates a presently preferred hardware configuration of an ECG module in accordance with the invention. As illustrated, the ECG signals from the respective electrodes LA, RA, LL, RL, CA, and/or CB are pulled up by pullup resistors 12 and buffered by amplifiers 14 before being processed in accordance with the techniques of the invention. The outputs of the respective amplifiers 14 are applied to an electrode status multiplexer 16, instrumentation amplifiers 18, and to circuitry for determining the common mode noise levels. Microprocessor 22 acquires electrode status information (STATUS) by configuring the electrode status multiplexer 16 with the STATUS SEL signal to output status information for a given electrode. The electrode status multiplexer 16 outputs the selected electrode status to A/D converter 20 for microprocessor 22 to process. In turn, each electrode is output to forma a combined electrode status. Instrumentation amplifiers 18, on the other hand, amplify the ECG waveform signals from the electrodes to the levels appropriate for the monitor's instrumentation, and the amplified ECG waveform signals are converted into digital signals by A/D converter 20 before being applied to microprocessor 22 for processing for display on ECG waveform display 24.

As will described below in more detail with respect to FIGS. 4 and 5, microprocessor 22 processes the STATUS signal from the electrode status multiplexer 16 to determine which electrodes are connected and which electrode to drive as the reference electrode as well as from which electrodes to receive the resulting ECG waveform signals. Depending upon which electrodes are connected, microprocessor 22 sends a limb select signal (LIMB SEL) to instrumentation amplifiers 18 and a limb lead select circuit 26. LIMB SEL is used to select outputs of a multiplexer in the instrumentation amplifiers 18 to determine which signals to amplify and output for further processing. The limb lead select circuit 26, on the other hand, uses LIMB SEL to select the limb leads from which an ECG common mode signal can be generated when using the standard three lead configuration.

In a preferred embodiment of the ECG module, the operator may select which ECG waveform to view from the multiple leads formed from the different combinations of differential electrode signals. Typically, in a three lead configuration for ECG lead II, the reference electrode is LA; therefore, limb lead select circuit 26 typically selects LL and RA. Of course, different combinations may be selected by the operator as desired. The ECG signals from the selected limb leads are then equally weighted and applied to a summer 28. The sum signal is applied as a first input (BASIC) to a common mode select circuit 30 for selecting the appropriate weighted sum for the common mode noise cancellation signal. Common mode select circuit 30 selects the weighted sum of the connected electrodes based on the determination by microprocessor 22 of the connected electrodes. A common mode drive signal based on the connected electrodes is then used to drive the reference electrode.

The different combinations of electrode outputs are applied to respective summers 32–38 to calculate common mode signals representative of the different possible combinations of detection electrodes providing ECG signals. In particular, the ECG signals from electrodes LA, RA, and LL are applied in equal weights to summer 32 to determine the so-called Wilson's Central Terminal (WCT) summation for a standard four lead configuration in which RL is the reference electrode. The sum WCT is applied as another common mode option for common mode select circuit 30. WCT is also applied to a summer 34 for summation with the equally weighted ECG signal from chest lead CB. The sum WCT+CB is applied as another common mode option to common mode select circuit 30. Similarly, WCT and the equally weighted ECG signal from chest lead CA are summed in summer 36, and WCT and the equally weighted ECG signals from CA and CB are summed in summer 38. The respective sums, WCT+CA and WCT+CA+CB, are applied as additional common mode options for common mode select circuit 30. Common mode select circuit 30 then selects one of the weighted sum inputs as the common mode signal depending upon a common mode select signal (CM SEL) received from microprocessor 22. CM SEL selects a common mode signal which corresponds to the actually connected electrodes so as to maximize performance by optimally correcting common mode interference in the outputs of the respective electrodes. The resulting common mode voltage is then output as a CM drive signal and applied via a buffer 40 to a common mode drive select circuit 42 for driving the reference electrode. The reference electrode is determined by microprocessor 22 in accordance with the flow diagram of FIG. 4, and a reference electrode select signal (REF SEL) is applied to common mode drive select circuit 42. Common mode drive select circuit 42 then applies the CM drive signal to the selected reference electrode via the appropriate lead.

Figure 4:
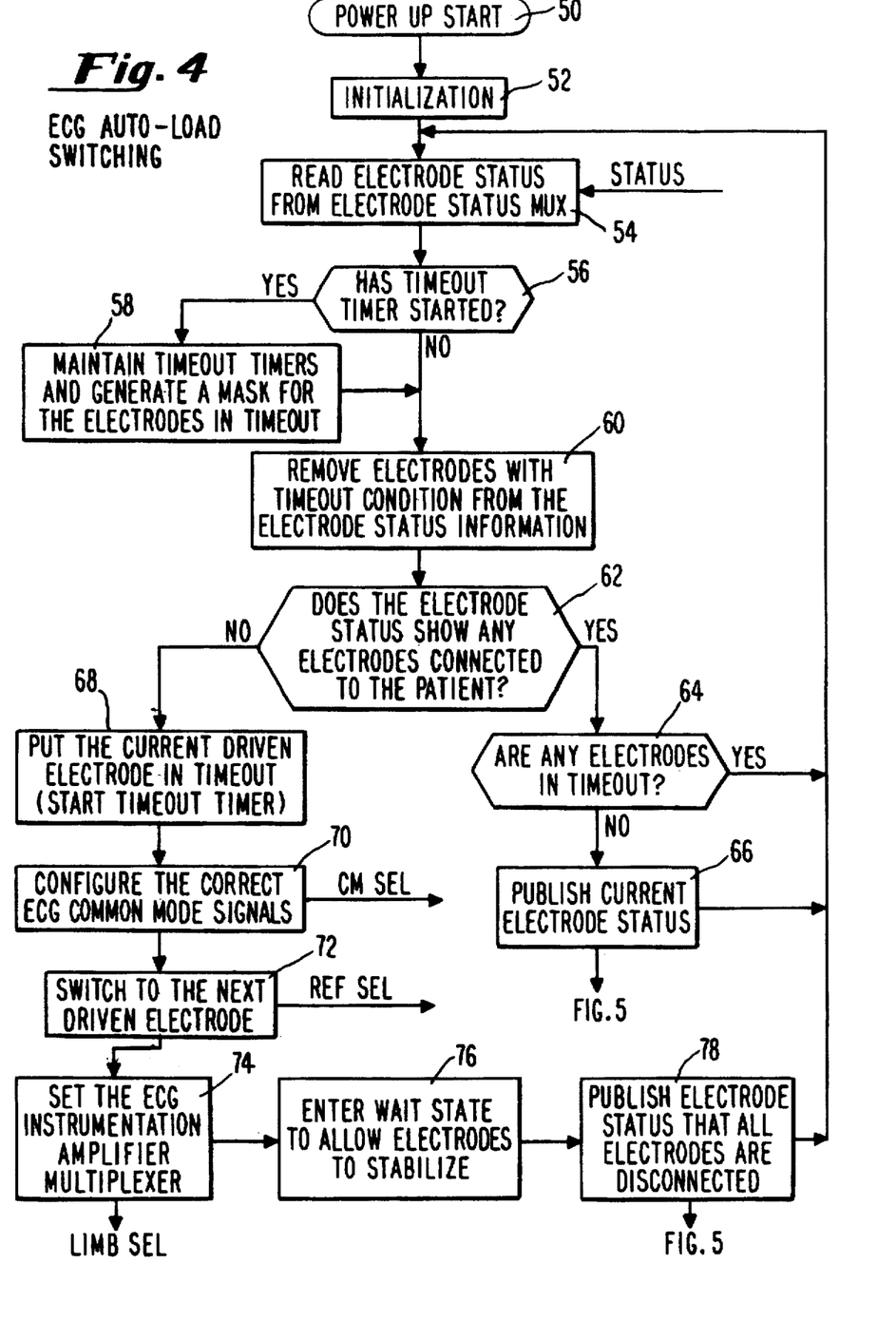
FIG. 4 is a flow diagram of the processing performed by the processor of FIG. 3 to determine which electrode(s) is/are connected to the patient.

FIG. 4 is a flow diagram of the processing performed by the processor of FIG. 3 to determine which electrodes are connected to the patient and to perform automatic reference lead switching, as appropriate. The software routine illustrated in FIG. 4 operates continuously and is entered at step 50 at power up and exited when power to the ECG module is turned off.

After power up at step 50, the registers of the microprocessor 22 are initialized at step 52. The microprocessor 22 then reads the combined electrode STATUS signals obtained from the electrode status multiplexer 16 (converted into digital form using A/D converter 20) at step 54 to determine if any of the electrodes have had a change in status (e.g., become disconnected). The electrode status is updated continually at frequent intervals. Microprocessor 22 then determines at step 56 whether a timeout timer has started in order to determine whether the reference (or driven) electrode has been switched recently. The timeout period starts after the switching of the reference electrode so that the status of the previous reference electrode can be disabled while the readings from the other electrodes are evaluated. If the timeout timer has started but not yet timed out, and the old reference electrode is still disabled, then the timeout timer is maintained at step 58 and the electrode status for that electrode is removed and ignored for the disabled electrode in timeout at step 60. Microprocessor 22 then determines at step 62 whether any of the electrodes remain connected to the patient. As noted above, if the reference electrode has been disconnected, it appears to the microprocessor 22 that all electrodes have been disconnected. However, if a signal is received from at least one of the electrodes, then it is known that the current reference electrode remains connected. In this case, microprocessor 22 proceeds to step 64 to determine if any of the electrodes remain in timeout. If so, the loop of steps 54-64 is repeated until the timeout period ends, at which time microprocessor proceeds to step 66 to publish a status update of the current electrodes. The change in status of the electrodes causes the software routine of FIG. 5 to begin in parallel with the software routine of FIG. 4. Microprocessor 22 then returns to step 54 to read the latest STATUS signal.

If it is determined at step 62 that no electrodes are connected to the patient, indicating that either all electrodes are disconnected or just the reference electrode is disconnected, microprocessor 22 proceeds to step 68, where the current reference electrode is placed in the timeout state by starting the timeout timer. The configuration for the correct ECG common mode signal for the remaining electrodes is then determined at step 70, and the CM SEL signal is sent to the common mode select circuit 30. The optimum common mode sum input into common mode select circuit 30 is selected in response to CM SEL and used to generate the CM drive signal for the new reference electrode. Microprocessor 22 then selects the new reference electrode at step 72 in accordance with a predetermined priority scheme and sends the REF SEL signal to common mode drive select circuit 42 to instruct it to apply the CM drive signal to the new reference electrode. Since the reference electrode is typically RL, microprocessor 22 first attempts to use chest lead CB as the new reference electrode. If this results in a status indicating that all electrodes are disconnected, the microprocessor 22 attempts to use chest lead CA as the new reference electrode. In turn, LL, RA, and LA are used as new reference electrodes until an electrode status indicates that there are electrodes connected. If none of these electrodes is connected, then no more than one electrode can be connected.

Once the microprocessor 22 has switched the reference electrode at step 72, an ECG instrumentation amplifier multiplexer of the instrumentation amplifiers 18 is set at step 74. The microprocessor 22 then enters a wait state at step 76 to allow the electrodes to stabilize to their new output levels and adapt to their new settings in response to the new reference electrode. Once the electrodes have stabilized, an electrode status is published at step 78 indicating that all electrodes are disconnected as determined at step 62. Once the status of the electrodes has been published at step 78, the software routine of FIG. 5 begins in parallel with the software routine of FIG. 4. Microprocessor 22 then returns to step 54 to read the latest STATUS signal.

Figure 5:
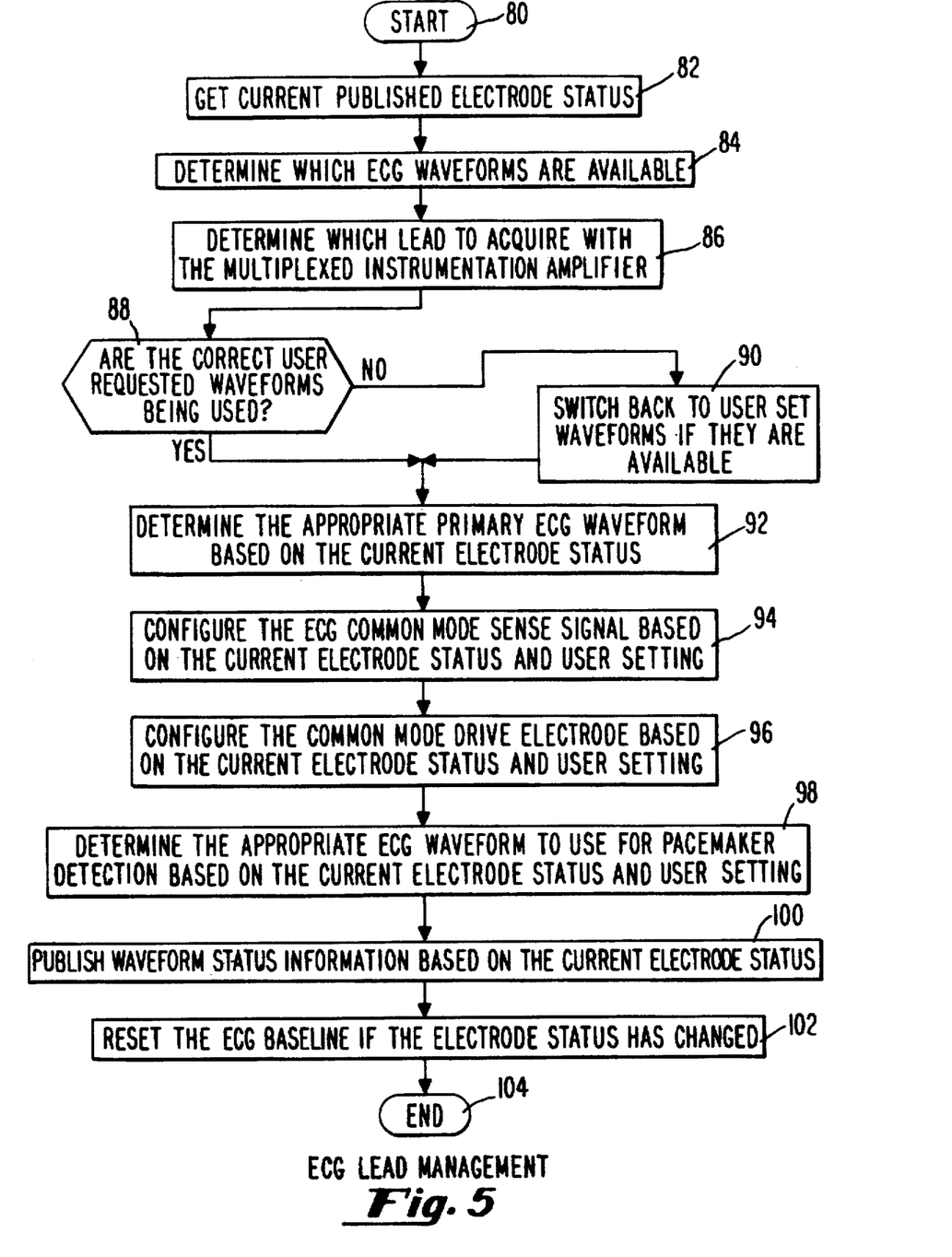
FIG. 5 is a flow diagram of the processing performed by the processor of FIG. 3 to interpret the electrode status to identify the appropriate hardware and software states necessary to restore preferred monitoring or to continue monitoring of the patient with a different set of ECG waveforms.

Once a valid electrode status is determined in the software routine of FIG. 4, the software routine of FIG. 5 begins to interpret the electrode status to identify the appropriate hardware and software states necessary to maintain preferred monitoring based on the electrodes connected to the patient. As illustrated in FIG. 5, the ECG lead management routine starts at step 80 and gets the current published electrode status from the software routine of FIG. 4 at step 82. Microprocessor 22 then determines at step 84 which ECG waveforms are available from the remaining electrodes, and at step 86 microprocessor 22 determines which lead to acquire with the multiplexed instrumentation amplifiers 18 to acquire certain ECG waveform data. Since the ECG module allows the operator to select the waveforms to be displayed, at step 88 microprocessor 22 determines if the waveforms requested by the operator are being displayed. If not, microprocessor 22 switches back to the operator selected waveforms, if available, at step 90. Microprocessor 22 then determines at step 92 the appropriate primary ECG waveform based on the current electrode status.

At step 94, microprocessor 22 configures the ECG common mode signal based on the current electrode status and operator settings or default settings so as to minimize transient noise as a result of changes in other settings and sends the CM SEL signal to the common mode select circuit 30. At step 96, the new common mode reference electrode is configured in accordance with the current electrode status and operator settings. Then, if the ECG module supports a pacemaker detection feature, at step 98, the appropriate ECG waveforms to use for pacemaker detection are determined based on the current electrode status and operator settings. Finally, at step 100, the ECG waveform status information is published based on the current electrode status and the ECG baseline is reset at step 102 if the electrode status has changed. The ECG lead management routine is then exited at step 104.

When the electrode status is published, the electrode status is preferably displayed as a status message to the operator on the ECG waveform display 24. ECG monitoring using the new reference electrode and the optimal lead configuration continues until complete electrode connection is regained. At that time, the ECG monitor of the invention automatically switches back to the preferred settings with the desired reference electrode and primary lead waveform. The ECG monitor of the invention thus maintains the ECG monitoring of the patient with an optimal lead configuration until such time that complete ECG electrode status is returned.

Although an exemplary embodiment of the invention has been described in detail above, those skilled in the art will readily appreciate that many additional modifications are possible in the exemplary embodiment without materially departing from the novel teachings and advantages of the invention. Accordingly, these and all such modifications are intended to be included within the scope of this invention as defined in the following claims.

What is claimed is:

1. An electrocardiogram (ECG) monitor for detecting and displaying an ECG waveform of a patient, comprising:

a plurality of electrodes including a reference electrode and at least two detecting electrodes which detect an ECG waveform of the patient;

electrode status detection means for detecting whether said detecting electrodes and reference electrode are connected to the patient and for generating electrode status signals;

reference lead switching means responsive to said electrode status signals for selecting a detecting electrode as a new reference electrode when said electrode status detection means detects that at least said reference electrode is not connected to the patient and for selecting electrodes of said plurality of electrodes to be used to generate a common mode drive signal for application to said new reference electrode; and means for processing ECG waveforms acquired from said detecting electrodes in response to application of a common mode drive signal to said new reference electrode and for displaying said ECG waveforms to an operator.

2. A monitor as in claim 1, further comprising a common mode signal generating circuit including means for generating sum signals from combinations of signals output by detecting electrodes and means responsive to said reference lead switching means for selecting a sum signal corresponding to the currently available detecting electrodes and for generating common mode drive signals for driving either said reference electrode or said new reference electrode.

3. A monitor as in claim 2, further comprising a common mode drive select circuit for applying a common mode drive signal from said common mode signal generating circuit to the electrode selected by said reference lead switching means as the new reference electrode.

4. A monitor as in claim 3, wherein said reference lead switching means comprises a microprocessor responsive to said electrode status signals to determine whether the reference electrode is connected to the patient and to select one of the detecting electrodes as the new reference electrode when it is determined that the reference electrode is not connected to the patient.

5. A monitor as in claim 4, wherein said microprocessor removes the reference electrode from the electrode status signals when the new reference electrode is selected.

6. A monitor as in claim 4, wherein said microprocessor sends a common mode drive select signal to said common mode drive signal generating circuit in accordance with the electrodes said microprocessor determines to be connected to the patient.

7. A monitor as in claim 4, wherein said microprocessor sends a reference electrode select signal to said common mode drive select circuit to instruct said common mode drive select circuit to apply said common mode drive signal to the new reference electrode.

8. A monitor as in claim 4, wherein said processing means comprises instrumentation amplifiers for amplifying ECG waveforms received from said detecting electrodes, and said microprocessor sends an ECG waveform select signal to said instrumentation amplifiers to select the ECG waveforms for display.

9. A modular patient monitor for monitoring selected vital signs of a patient, said patient monitor comprising at least one removable electronic module for processing vital signs data from said patient and a display for displaying the processed vital signs data, wherein said at least one removable electronic module comprises an electrocardiogram (ECG) module which detects and processes ECG waveforms received from a plurality of electrodes including a reference electrode and at least two detecting electrodes which detect an ECG waveform of the patient, said ECG module comprising:

electrode status detection means for detecting whether said detecting electrodes and reference electrode are connected to the patient and for generating electrode status signals;

reference lead switching means responsive to said electrode status signals for selecting a detecting electrode as a new reference electrode when said electrode status detection means detects that at least said reference electrode is not connected to the patient and for selecting electrodes of said plurality of electrodes to be used to generate a common mode drive signal for application to said new reference electrode; and means for processing ECG waveforms acquired from said detecting electrodes in response to application of a common mode drive signal to said new reference electrode and for displaying said ECG waveforms to an operator.

10. A monitor as in claim 9, said ECG module further comprising a common mode signal generating circuit including means for generating sum signals from combinations of signals output by detecting electrodes and means responsive to said reference lead switching means for selecting a sum signal corresponding to the currently available detecting electrodes and for generating common mode drive signals for driving either said reference electrode or said new reference electrode.

11. A monitor as in claim 10, said ECG module further comprising a common mode drive select circuit for applying a common mode drive signal from said common mode signal generating circuit to the electrode selected by said reference lead switching means as the new reference electrode.

12. A monitor as in claim 11, wherein said reference lead switching means comprises a microprocessor responsive to said electrode status signals to determine whether the reference electrode is connected to the patient and to select one of the detecting electrodes as the new reference electrode when it is determined that the reference electrode is not connected to the patient.

13. A monitor as in claim 12, wherein said microprocessor removes the reference electrode from the electrode status signals when the new reference electrode is selected.

14. A monitor as in claim 12, wherein said microprocessor sends a common mode drive select signal to said common mode drive signal generating circuit in accordance with the electrodes said microprocessor determines to be connected to the patient.

15. A monitor as in claim 12, wherein said microprocessor sends a reference electrode select signal to said common mode drive select circuit to instruct said common mode drive select circuit to apply said common mode drive signal to the new reference electrode.

16. A monitor as in claim 12, wherein said processing means comprises instrumentation amplifiers for amplifying ECG waveforms received from said detecting electrodes, and said microprocessor sends an ECG waveform select signal to said instrumentation amplifiers to select the ECG waveforms for display to the operator on said display.

17. A method of detecting an ECG waveform of a patient, comprising the steps of:

applying a plurality of electrodes to the patient, the electrodes including a reference electrode and at least two detecting electrodes which detect an ECG waveform of the patient;

applying a drive signal to the reference electrode;

detecting whether said detecting electrodes and reference electrode are connected to the patient;

selecting a detecting electrode as a new reference electrode when it is determined in said detecting step that at least said reference electrode is not connected to the patient; and applying a new drive signal to the new reference electrode.

18. A method as in claim 17, comprising the further steps of generating sum signals of the ECG waveforms received from combinations of detecting electrodes available after said selecting step, selecting a sum signal corresponding to the ECG waveforms from the detecting electrodes available after said selecting step, and generating common mode drive signals for driving said new reference electrode in said new drive signal applying step.

19. A method as in claim 17, wherein said detecting step comprises the step of determining which detecting electrodes are outputting ECG waveforms and said selecting step comprises the steps of determining whether the reference electrode is connected to the patient and selecting one of the detecting electrodes as the new reference electrode when it is determined that the reference electrode is not connected to the patient.

20. A method as in claim 17, comprising the further steps of indicating to an operator which electrodes are connected to the patient and displaying the ECG waveforms desired by the operator, if such waveforms are available.

* * * * *

UNITED STATES PATENT AND TRADEMARK OFFICE
CERTIFICATE OF CORRECTION

PATENT NO. : 5,788,644
DATED : August 4, 1998
INVENTOR(S) : Robert F. Donehoo, et al It is certified that error appears in the above-identified patent and that said Letters Patent is hereby corrected as shown below:

Col. 8, line 29, after "display" insert --to the operator--.

Signed and Sealed this

Fifteenth Day of December, 1998

*Attest:*

BRUCE LEHMAN

*Attesting Officer*   Commissioner of Patents and Trademarks